United States Patent [19]

Sanders

[11] Patent Number: 5,470,860

[45] Date of Patent: Nov. 28, 1995

[54] 1,4-DIHYDROPYRIDINES FOR USE IN THE TREATMENT OF DERMATOSES

[75] Inventor: Karl Sanders, Konstanz, Germany

[73] Assignee: Byk Gulden Lomberg Chemische Fabrik GmbH, Konstanz, Germany

[21] Appl. No.: 244,887

[22] PCT Filed: Dec. 4, 1992

[86] PCT No.: PCT/EP92/02807

§ 371 Date: Jun. 13, 1994

§ 102(e) Date: Jun. 13, 1994

[87] PCT Pub. No.: WO93/11766

PCT Pub. Date: Jun. 24, 1994

[30] Foreign Application Priority Data

Dec. 13, 1991 [CH] Switzerland .......................... 03671/91

[51] Int. Cl.⁶ ...................... A61K 31/445; A61K 31/495
[52] U.S. Cl. ........................... 514/318; 514/252; 514/253
[58] Field of Search ..................................... 514/318, 252, 514/253

[56] References Cited

U.S. PATENT DOCUMENTS 4,994,461  2/1991  Ulrich ..................................... 514/318
5,326,772  7/1994  Klemm et al. .......................... 514/318

Primary Examiner—Raymond Henley, III
Attorney, Agent, or Firm—Jacobson, Price, Holman & Stern

[57] ABSTRACT

The invention relates to the use of 1,4-dihydropyridines of the formula (I), in which the substituents and symbols are as defined in the description, for the preparation of medicaments for the treatment of dermatoses.

16 Claims, 1 Drawing Sheet

1,4-DIHYDROPYRIDINES FOR USE IN THE TREATMENT OF DERMATOSES

This application is a 371 of PCT/EP92/02807 filed Dec. 4, 1992.

TECHNICAL FIELD

The invention relates to the new use of known dihydropyridines for the preparation of medicaments for the treatment of dermatoses.

PRIOR ART

A series of patent applications and patents describes the suitability of compounds from various classes of substance for the treatment of skin diseases. For example, it is said that certain xanthine derivatives (see e.g. EP 389 282, EP 267 676, EP 260 127, WO 87/04435 and EP 195 496) and certain imidazo-quinazoline derivatives (see e.g. U.S. Pat. No. 4,837,239, U.S. Pat. No. 4,690,925, U.S. Pat. No. 4,663,320, EP 212 647, EP 153 152 and EP 116 948) are suitable for the treatment of inflammatory skin diseases. European Patent Application EP-A-296 316 describes enantiomerically pure 1,4-dihydropyridines as effective vasodilators with coronary-therapeutic properties.

DESCRIPTION OF THE INVENTION

It has now been found that the 1,4-dihydropyridines described in more detail below are outstandingly suitable for the treatment of dermatoses.

Figure 1:
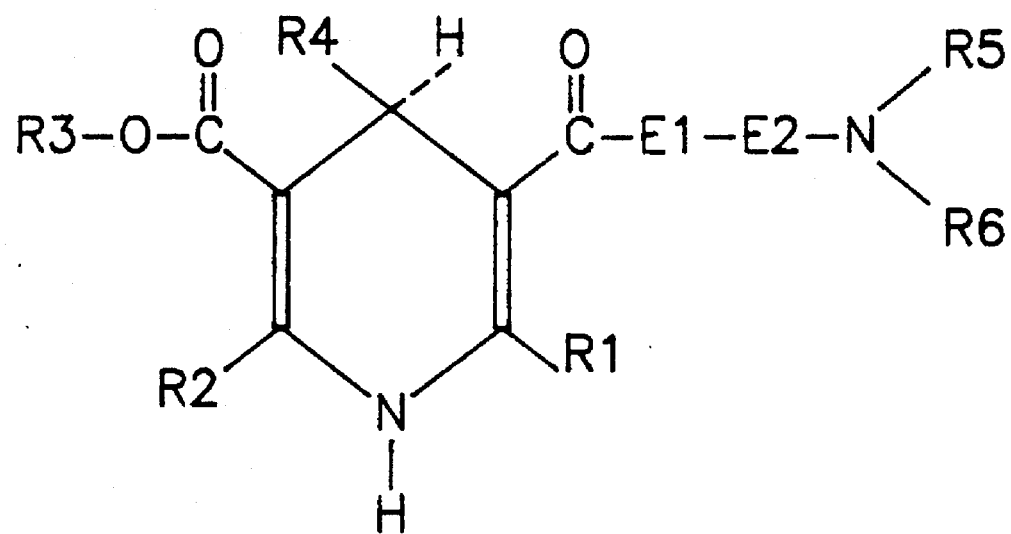
FIGS. 1 and 1a represent the general structure of the compound employed herein (Formula I) and of the moiety formed by R5 and R6 defined below (Formula Ia).
Figure 1A:
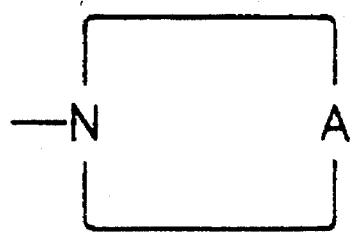

The invention therefore relates to the use of 1,4-dihydropyridines of the formula I (see formula sheet attached as FIG. 1), in which R1 is 1–6C-alkyl or 1–4C-alkoxy-2–4C-alkyl, R2 is hydrogen, amino ($NH_2$), 1–6C-alkyl or 1–4C-alkoxy-2–4C-alkyl, R3 is 1–6C-alkyl or 1–4C-alkoxy-2–4C-alkyl, R4 is phenyl substituted by R41 and R42, R41 is hydrogen, hydroxyl, halogen, nitro, cyano, trifluoromethyl, 1–4C-alkyl, 1–4C-alkoxy, 1–4C-alkoxy which is substituted completely or partially by fluorine, 1–4C-alkoxycarbonyl, 2–5C-acyl, amino, or mono- or di-1–4C-alkylamino, R42 is hydrogen, hydroxyl, halogen, nitro, cyano, trifluoromethyl, 1–4C-alkyl, 1–4C-alkoxy, 1–4C-alkoxy which is substituted completely or partially by fluorine, 1–4C-alkoxycarbonyl, 2–5C-acyl, amino, or mono- or di-1–4C-alkylamino, E1 is oxygen (O), E2 is straight-chain or branched 1–5C-alkylene, the group —$(CH_2)_m$—E—$(CH_2)_n$— or the group —A1—O—A2—, E is vinylene (—CH=C—) or ethynylene (—C≡C—), m is 1 or 2, n is 1 or 2, A1 is 2–4C-alkylene, A2 is 2–4C-alkylene or 2C-alkyleneoxy-2C-alkylene, R5 and R6 together, including the nitrogen atom to which both are attacked, are a radical of the formula Ia (see formula sheet attached as FIG. 1), in which A is —$CH_2$—$CH_2$—C(R7)R8—$CH_2$—$CH_2$—, —$CH_2$—$CH_2$—CHR9—$CH_2$—$CH_2$— or —$CH_2$—$CH_2$—$CH_2$—CHR10—, R7 is hydrogen (H) or aryl and R8 is aryl, or R7 and R8 together are diarylmethylene, R9 is diaryl-1–4C-alkyl, and R10 is aryl-1–4C-alkyl, wherein aryl is phenyl which is substituted by R11 and R12, and where R11 and R12 are identical or different and are hydrogen (H), 1–4C-alkyl, 1–4C-alkoxy, halogen, hydroxyl, trifluoromethyl or together are methylenedioxy, and their pharmacologically acceptable salts, for the preparation of medicaments for the treatment of dermatoses.

1–6C-alkyl is straight-chain or branched and is, for example, a hexyl, neopentyl, isopentyl, butyl, isobutyl, sec-butyl, tert-butyl, propyl, isopropyl or, in particular, an ethyl or methyl radical.

1–4C-alkyl is straight-chain or branched and is, for example, a butyl, isobutyl, sec-butyl, tert-butyl, propyl, isopropyl, ethyl or, in particular, a methyl radical.

1–4C-alkoxy contains, in addition to the oxygen atom, one of the abovementioned 1–4C-alkyl radicals. The methoxy and ethoxy radical are preferred.

1–4C-alkoxy-2–4C-alkyl is a butyl, propyl or, in particular, an ethyl radical, which is substituted by one of the abovementioned 1–4C-alkoxy radicals. The methoxyethyl radical is preferred.

Halogen in the context of the invention is bromine, fluorine and, in particular, chlorine.

1–4C-alkoxy substituted completely or partially by fluorine is, for example, 1,1,2,2-tetrafluoroethoxy, trifluoromethoxy, 2,2,2-trifluoroethoxy or, in particular, difluoromethoxy.

1–4C-alkoxycarbonyl contains, in addition to the carbonyl group, one of the abovementioned 1–4C-alkoxy radicals.

2–5C-acyl contains, in addition to the carbonyl group, one of the abovementioned 1–4C-alkyl radicals. The acetyl radical is preferred.

Mono- or di-1–4C-alkylamino contains, in addition to the nitrogen atom, one or two of the abovementioned 1–4C-alkyl radicals. Di-1–4C-alkylamino is preferred, particular preference in this case being given to dimethyl-, diethyl- or diisopropylamino.

Straight-chain or branched 1–5C-alkylene is, for example, methylene (—$CH_2$—), ethylene (—$CH_2$—$CH_2$—), trimethylene (—$CH_2$—$CH_2$—$CH_2$—), tetramethylene (—$CH_2$—$CH_2$—$C_2$—$CH_2$—), 1,2-dimethylethylene [—CH($CH_3$)—CH($CH_3$)—], 1,1-dimethylethylene [—C($CH_3$)$_2$—$CH_2$—], 1,1-dimethylpropylene [—C($CH_3$)$_2$—$CH_2$—$CH_2$—], 2,2-dimethylethylene [—$CH_2$—C($CH_3$)$_2$—], isopropylidene [—C($CH_3$)$_2$—] and 1-methylethylene [—CH($CH_3$)—$CH_2$—].

2–4C-alkylene is ethylene (—$CH_2$—$CH_2$—), trimethylene (—$CH_2$—$CH_2$—$CH_2$—) and tetramethylene (—$CH_2$—$CH_2$—$CH_2$—$CH_2$—), with ethylene being preferred.

2C-alkyleneoxy-2C-alkylene is ethylene substituted by ethyleneoxy (—$CH_2$—$CH_2$—O—$CH_2$—$CH_2$—).

Aryl is phenyl which is substituted by R11 and R12. Examples of aryl radicals which can be mentioned are the radicals: phenyl, 4-methoxyphenyl, 4-chlorophenyl, 4-methylphenyl, 4-fluorophenyl, 3-fluorophenyl, 3-chlorophenyl, 2-chlorophenyl, 3-methoxyphenyl, 2-methoxyphenyl, 2-ethoxyphenyl, 2-methylphenyl, 3-chloro-4-methylphenyl, 3,4-dichlorophenyl, 3,6-dichlorophenyl, 2,4-dimethylphenyl, 2,6-dimethylphenyl, 3,4-dimethylphenyl, 3,4-methylenedioxyphenyl, 2-trifluoromethylphenyl and 3-trifluoromethylphenyl.

Diaryl-1–4C-alkyl is 1–4C-alkyl which is substituted by two aryl radicals. Diaryl-1–4C-alkyl is, in particular, diphenylethyl (benzhydryl), or substituted benzhydryl such as, for example, 4,4'-difluorobenzhydryl, 4,4'-dimethylbenzhydryl, 4,4'-dimethoxybenzhydryl or 4,4'-dichlorobenzhydryl.

Aryl-1–4C-alkyl is 1–4C-alkyl which is substituted by aryl. Benzyl and 4-chlorobenzyl may be mentioned in particular.

Suitable salts are all those pharmacologically acceptable salts with inorganic and organic acids which are customarily used in the pharmaceutical industry. Examples of suitable such salts are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, (2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, and in the preparation of the salt the acids—depending on whether they are monobasic or polybasic aids and on which salt is desired—are employed in an equimolar ratio or in one which deviates from this.

The medicaments are prepared by methods which are known per se and which are familiar to the person skilled in the art. As medicaments the pharmacologically active compounds (=active substances) are employed either as such or, preferably, in combination with appropriate pharmaceutical auxiliaries or excipients in the form of tablets, coated tablets, capsules, suppositories, patches (e.g. as a TTS), emulsions, suspensions or solutions, the content of active substance being advantageously between 0.1 and 95%.

On the basis of his or her expert knowledge, the person skilled in the art will be aware of which auxiliaries and/or excipients are appropriate for the desired pharmaceutical formulations. In addition to solvents, gel formers, suppository bases, tablet auxiliaries and other active substance carriers it is possible, for example, to use antioxidants, dispersants, emulsifiers, anti-foaming agents, flavor correctors, preservatives, solubilizers, colorants or, in particular, permeation promoters and complexing agents (e.g. cyclodextrins).

The active substances can be administered orally, parenterally or percutaneously in a daily dose of from approximately 0.5 to approximately 30 mg/kg of body weight, if desired in the form of two or more, preferably 1 to 4 doses in order to achieve the desired effect. In the case of parenteral treatment, the dosages which may be employed are similar or (especially in the case of intravenous administration of the active substances), in general, lower. The optimum dosage and method of administration of the active substances that are necessary in each case can be determined by every person skilled in the art on the basis of their expert knowledge.

The compounds of the formula I are employed, in particular, in the form of those medicaments which are suitable for topical application. For the preparation of the medicaments the compounds of the formula I and/or their pharmacologically acceptable salts (=active substances) are preferably mixed with suitable pharmaceutical auxiliaries and processed further to give appropriate pharmaceutical formulations. Examples of suitable pharmaceutical formulations are powders, emulsions, suspensions, sprays, oils, ointments, fatty ointments, creams, pastes, gels or solutions, in which the content of active substance is advantageously between 0.1 and 99%.

Examples of dermatoses which may be mentioned are inflammatory and allergic skin diseases and, in particular, those skin diseases which result from pathologically increased cell reproduction. For example, the compounds of the formula I can be employed for preventing and treating the following skin diseases: psoriasis vulgaris, toxic and allergic contact eczema, atopic eczema, seborrheic eczema, follicular and extensive pyoderma, endogenous and exogenous acne, acne rosacea and other inflammatory and allergic skin diseases. The invention thus further relates to the use of compounds of the formula I and their pharmacologically acceptable salts for the treatment of those individuals suffering from dermatoses.

The low calcium channel-blocking activity of compounds of the formula I, which is evident in the comparatively low effect of these compounds on the cardiovascular system, for example on blood pressure and heart rate, permits the use of compounds of the formula I and of their salts in human medicine as potent agents for the treatment of dermatoses, for example of psoriasis. In contrast to the calcium channel blockers, which have a pronounced cardiovascular effect, compounds of the formula I and their salts can be administered in therapeutically effective doses without the danger of unwanted side-effects on the cardiovascular system.

One embodiment (embodiment a) of the invention is the use of 1,4-dihydropyridines of the formula I, in which E2 is straight-chain or branched 1–5C-alkylene or the group —A1—O—A2—, A is —CH$_2$—CH$_2$—C(R7)R8—CH$_2$—CH$_2$—, R7 is aryl, R8 is aryl, and R1, R2, R3, R4, R41, R42, E1, A1, A2, R5 and R6 are as defined above, and their pharmacologically acceptable salts, for the preparation of medicaments for the treatment of dermatoses.

A further embodiment (embodiment b) of the invention is the use of 1,4-dihydropyridines of the formula I, in which E2 is the group —(CH$_2$)$_m$—E—(CH$_2$)$_n$— and R1, R2, R3, R4, R41, R42, E1, E, m, n, R5, R6, A, R7, R8, R9 and R10 areas defined above, and their pharmacologically acceptable salts, for the preparation of medicaments for the treatment of dermatoses.

A further embodiment (embodiment c) of the invention is the use of 1,4-dihydropyridines of the formula I, in which R7 is hydrogen (H) and R8 is aryl, or R7 and R8 together are diarylmethylene, and R1, R2, R3, R4, R41, R42, E1, E2, E, m, n, A1, A2, R5, R6, A, R9 and R10 are as defined above, and their pharmacologically acceptable salts, for the preparation of medicaments for the treatment of dermatoses.

The invention relates in particular to the use according to the invention of compounds of the formula I in which R1 is 1–4C-alkyl, R2 is 1–4C-alkyl, R3 is 1–4C-alkyl, R4 is phenyl substituted by R41 and R42, R41 is hydrogen, chlorine or nitro, R42 is hydrogen or chlorine, E1 is oxygen, E2 is ethylene or propylene, R5 and R6 together, including the nitrogen atom to which both are attached, are a radical of the formula Ia in which A is —CH₂—CH₂—C(R7)R8—CH₂—CH₂—, —CH₂—CH₂—CHR 9—CH₂CH₂— or —CH₂—CH₂—CH₂—CHR10—, R7 is hydrogen or phenyl, and R8 is phenyl, or R7 and R8 together are diphenylmethylene, R9 is diphenylmethyl (benzhydryl), and R10 is benzyl or 4-chlorobenzyl, and their pharmacologically acceptable salts.

The invention relates very particularly to the use according to the invention of compounds of embodiments a, b and c, in which the substituents and symbols have the definitions given for the particular subject of the invention.

The invention relates preferably to the use according to the invention of compounds of the formula I in which R1 is 1–4C-alkyl, R2 is 1–4C-alkyl, R3 is 1–4C-alkyl, R4 is 3-nitrophenyl, E1 is oxygen, E2 is ethylene or propylene, R5 and R6 together, including the nitrogen atom to which both are attached, are a radical of the formula Ia in which A is —CH₂—CH₂—C(R7)R8—CH₂—CH₂—, R7 is phenyl, and R8 is phenyl, and their pharmacologically acceptable salts.

Compounds which are particularly suitable for the use according to the invention are evident from the following Table 1, in which the corresponding compounds of the formula I (see formula sheet attached) are defined on the basis of the definitions of their substituents (Ph is the phenyl radical):

human keratinocytes.

To determine the action, firstly human keratinocytes from the preputial skin of neonates after the 1st passage are distributed in MCDB153 medium in 96-well microtiter plates ($2 \times 10^3$ cells/well) and the compound given below is added in concentrations of from $10^{-10}$ to $10^{-5}$M, blank controls containing only the solubilizer DMSO (1%). The period of incubation is 11 days, and after another 2 days in each case there is a change of medium followed by renewed addition of substance.

To determine the rate of cell reproduction, incubation is carried out for 1 h with 4-methylumbelliferyl heptanoate (MUH) according to the method described by R. Stadler et al., Journal of Investigative Dermatology 93, 532–534, 1989, after which the fluorescence intensity is measured using a Titertek Fluoroskan.

4 experiments were carried out, in each case with 4 wells/concentration. After evaluation of the measured results, for the compound 3-methyl 5-[3-(4,4-diphenyl-1-piperidyl)propyl] (−)-1,4-dihydro-2,6-dimethyl-4-(3-nitrophenyl)pyridine-3,5-dicarboxylate (=compound No. 1) after 11 days of incubation with normal keratinocytes an average inhibitory concentration ($IC_{50}$) of $8.8 \times 10^{-8}$M can be derived.

In a second cell reproduction test, human transformed keratinocytes (HaCat) are employed which are cultured in DMEM culture medium with an addition of 10% calf serum. Cells which have grown to confluence beforehand are isolated with trypsin and distributed in 6-well plates in a density of $40 \times 10^3$.

The test substance is added 24 h after distribution and after incubation for a further 72 h the cell count is determined using a Coulter counter. Controls are incubated without further additions or with the addition of the solubilizer polyethylene glycol 400 (0.05%).

Evaluation was made in each case for 6 wells/concentration.

Table 2 indicates by way of example the inhibitory effects of compound No. 1 on the cell reproduction of human transformed keratinocytes in culture.

TABLE 1

| R1 | R2 | R3 | R4 | —E1—E2— | —N(R5) R6 |
|---|---|---|---|---|---|
| CH₃ | CH₃ | CH₃ | 3-NO₂—Ph | —O—CH₂—CH₂—CH₂— | 4,4-di-Ph-piperidino |
| CH₃ | CH₃ | CH₃ | 2,3-di-Cl—Ph | —O—CH₂—CH₂—CH₂— | 4,4-di-Ph-piperidino |
| CH₃ | CH₃ | CH₃ | 2-Cl—Ph | —O—CH₂—CH₂—CH₂— | 4,4-di-Ph-piperidino |
| CH₃ | CH₃ | CH₃ | 3-NO₂—Ph | —O—CH₂—CH₂— | 4,4-di-Ph-piperidino |
| CH₃ | CH₃ | CH₃ | 3-NO₂—Ph | —O—CH₂—CH₂—CH₂— | 4-di-Ph-methylene-piperidino |
| CH₃ | CH₃ | CH₃ | 3-NO₂—Ph | —O—CH₂—CH₂—CH₂— | 4-Ph-piperidino |
| CH₃ | CH₃ | CH₃ | 3-NO₂—Ph | —O—CH₂—CH₂—CH₂— | 4-benzhydryl-piperidino |
| CH₃ | CH₃ | CH₃ | 3-NO₂—Ph | —O—CH₂—CH₂—CH₂— | 2-benzylpyrrolidino |
| CH₃ | CH₃ | CH₃ | 3-NO₂—Ph | —O—CH₂—CH=CH—CH₂— | 4,4-di-Ph-piperidino |
| CH₃ | CH₃ | CH₃ | 3-NO₂—Ph |  | 4,4-di-Ph-piperidino |
| CH₃ | CH₃ | CH₃ | 3-NO₂—Ph | —O—(CH₂)₂O(CH₂)₂— | 4,4-di-Ph-piperidino |

The compounds of the formula I are known, for example from EP-A-242 829, EP-A-296 316, DE-A 3 27 742 and WO 88/07531.

Pharmacology

The suitability of the compounds of the formula I for the treatment of psoriasis can be demonstrated on cultures of

TABLE 2

Effect on the growth of human transformed keratinocytes (HaCat) in culture.

| Concentration | Cell count (x ± SD) | % inhibition of growth |
| --- | --- | --- |
| Control | 324,724 ± 10,424 | |
| Compound 1, $10^{-6}$M | 128,865 ± 44,660 | 60 |
| Compound 1, $10^{-5}$M | 11,886 ± 2,942 | 96 |

From these measurements it is possible to derive for the compound No. 1, following 3 days of incubation with transformed keratinocytes, an inhibitory concentration ($IC_{50}$) of $0.52 \times 10^{-6}$M in comparison with the solvent control.

I claim:

1. A method of treating an amenable dermatosis by administering to a subject so afflicted an effective amount of a pharmaceutical composition comprising active component and pharmacologically-acceptable carrier therefor, wherein the active component is a 1,4-dihydropyridine of the formula

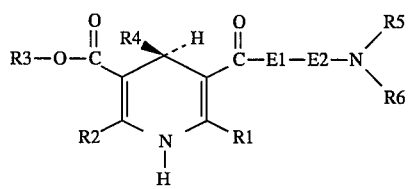

(I)

in which

R1 is 1–6C-alkyl or 1–4C-alkoxy-2–4C-alkyl,

R2 is hydrogen, amino ($NH_2$), 1–6C-alkyl or 1–4C-alkoxy-2–4C-alkyl,

R3 is 1–6C-alkyl or 1–4C-alkoxy-2–4C-alkyl,

R4 is phenyl substituted by R41 and R42,

R41 is hydrogen, hydroxyl, halogen, nitro, cyano, trifluoromethyl, 1–4C-alkyl, 1–4C-alkoxy, 1–4C-alkoxy which is substituted completely or partially by fluorine, 1–4C-alkoxycarbonyl, 2–5C-acyl, amino, or mono- or di-1–4C-alkylamino, R42 is hydrogen, hydroxyl, halogen, nitro, cyano, trifluoromethyl, 1–4C-alkyl, 1–4C-alkoxy, 1–4C-alkoxy which is substituted completely or partially by fluorine, 1–4C-alkoxycarbonyl, 2–5C-acyl, amino, or mono- or di-1–4C-alkylamino, E1 is oxygen (O), E2 is straight-chain or branched 1–5C-alkylene, the group —$(CH_2)_m$—E—$(CH_2)_n$— or the group —A1—O—A2—, E is vinylene (—CH=CH—) or ethynylene (—C≡C—), m is 1 or 2, n is 1 or 2, A1 is 2–4C-alkylene, A2 is 2–4C-alkylene or 2C-alkyleneoxy-2C-alkylene, R5 and R6 together, including the nitrogen atom to which both are attached, are a radical of the formula Ia

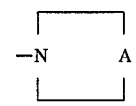

(Ia)

in which

A is —$CH_2$—$CH_2$—C(R7)R8—$CH_2$—$CH_2$—, —$CH_2$—$CH_2$—CHR9—$CH_2$—$CH_2$— or —$CH_2$—$CH_2$—$CH_2$—CHR10—,

R7 is hydrogen (H) or aryl and

R8 is aryl, or

R7 and R8 together are diarylmethylene,

R9 is diaryl-1–4C-alkyl, and

R10 is aryl-1–4C-alkyl, wherein aryl is phenyl which is substituted by R11 and R12, and where R11 and R12 are identical or different and are hydrogen (H), 1–4C-alkyl, 1–4C-alkoxy, halogen, hydroxyl, trifluoromethyl or together are methylenedioxy, or a pharmacologically-acceptable salt thereof.

2. A method of claim 1 in which

E2 is straight-chain or branched 1–5C-alkylene or the group —A1—O—A2—,

A is —$CH_2$—$CH_2$—C(R7)R8—$CH_2$—$CH_2$—,

R7 is aryl,

R8 is aryl, and

R1, R2, R3, R4, R41, R42, E1, A1, A2, R5 and R6 are as defined in claim 1, or a pharmacologically acceptable salt thereof.

3. A method of claim 1 in which

E2 is the group —$(CH_2)_m$—E—$(CH_2)_n$— and

R1, R2, R3, R4, R41, R42, E1, E, m, n, R5, R6, A, R7, R8, R9 and R10 are as defined in claim 1 or pharmacologically acceptable salt thereof.

4. A method of claim 1 in which

R7 is hydrogen (H) and

R8 is aryl, or

R7 and R8 together are diarylmethylene, and R1, R2, R3, R4, R41, R42, E1, E2, E, m., n, A1, A2, R5, R6, A, and R10 are as defined in claim 1, or a pharmacologically acceptable salt thereof.

5. A method of claim 1 in which

R1 is 1–4C-alkyl,

R2 is 1–4C-alkyl,

R3 is 1–4C-alkyl,

R4 is phenyl substituted by R41 and R42,

R41 is hydrogen, chlorine or nitro,

R42 is hydrogen or chlorine,

E1 is oxygen,

E2 is ethylene or propylene,

R5 and R6 together, including the nitrogen atom to which both are attached, are a radical of the formula Ia in which A is —$CH_2$—$CH_2$—C(R7)R8—$CH_2$—$CH_2$—, —$CH_2$—$CH_2$—CHR 9—$CH_2$—$CH_2$— or —$CH_2$—$CH_2$—$CH_2$—CHR10—, R7 is hydrogen or phenyl, and R8 is phenyl, or R7 and R8 together are diphenylmethylene, R9 is diphenylmethyl (benzhydryl), and R10 is benzyl or 4-chlorobenzyl, or a pharmacologically acceptable salt thereof.

6. A method of claim 1 in which

R1 is 1–4C-aklyl,

R2 is 1–4C-alkyl,

R3 is 1–4C-alkyl,

R4 is 3-nitrophenyl,

E1 is oxygen,

E2 is ethylene or propylene,

R5 and R6 together, including the nitrogen atom in which both are attached, are a radical of the formula Ia in which A is —CH$_2$—CH$_2$—C(R7)R8—CH$_2$—CH$_2$—, R7 is phenyl, R8 is phenyl, or a pharmacologically acceptable salt thereof.

7. A method of claim 1 wherein the active component is 3-methyl 5-[3-(4,4-diphenyl-1-piperidyl)propyl](+)-1,4-dihydro-2,6-dimethyl-4-(3-nitrophenyl)pyridine-3,5-dicarboxylate or a pharmacologically acceptable salt thereof.

8. A method of claim 1 for treating psoriasis.

9. A method of claim 1 wherein the dermatosis is a skin disease which results from pathologically increased cell reproduction.

10. A method of claim 1 wherein the dermatosis is a member selected from the group consisting of psoriasis vulgaris, toxic and allergic contact eczema, atopic eczema, seborrheic eczema, follicular and extensive pyoderma, endogenous and exogenous acne, acne rosacea and another inflammatory or allergic skin disease.

11. A method of claim 2 wherein the dermatosis is a member selected from the group consisting of psoriasis vulgaris, toxic and allergic contact eczema, atopic eczema, seborrheic eczema, follicular and extensive pyoderma, endogenous and exogenous acne, acne rosacea and another inflammatory or allergic skin disease.

12. A method of claim 3 wherein the dermatosis is a member selected from the group consisting of psoriasis vulgaris, toxic and allergic contact eczema, atopic eczema, seborrheic eczema, follicular and extensive pyoderma, endogenous and exogenous acne, acne rosacea and another inflammatory or allergic skin disease.

13. A method of claim 4 wherein the dermatosis is a member selected from the group consisting of psoriasis vulgaris, toxic and allergic contact eczema, atopic eczema, seborrheic eczema, follicular and extensive pyoderma, endogenous and exogenous acne, acne rosacea and another inflammatory or allergic skin disease.

14. A method of claim 5 wherein the dermatosis is a member selected from the group consisting of psoriasis vulgaris, toxic and allergic contact eczema, atopic eczema, seborrheic eczema, follicular and extensive pyoderma, endogenous and exogenous acne, acne rosacea and another inflammatory or allergic skin disease.

15. A method of claim 6 wherein the dermatosis is a member selected from the group consisting of psoriasis vulgaris, toxic and allergic contact eczema, atopic eczema, seborrheic eczema, follicular and extensive pyoderma, endogenous and exogenous acne, acne rosacea and another inflammatory or allergic skin disease.

16. A method of claim 7 wherein the dermatosis is a member selected from the group consisting of psoriasis vulgaris, toxic and allergic contact eczema, atopic eczema, seborrheic eczema, follicular and extensive pyoderma, endogenous and exogenous acne, acne rosacea and another inflammatory or allergic skin disease.

* * * * *